United States Patent [19]

Matsuura

[11] Patent Number: 5,239,115
[45] Date of Patent: Aug. 24, 1993

[54] METHOD FOR PRODUCING METHACRYLIC ACID

[75] Inventor: Ikuya Matsuura, Toyama, Japan

[73] Assignee: Nippon Shokubai Co., Ltd., Osaka, Japan

[21] Appl. No.: 775,965

[22] PCT Filed: Mar. 11, 1991

[86] PCT No.: PCT/JP91/00330
§ 371 Date: Oct. 31, 1991
§ 102(e) Date: Oct. 31, 1991

[87] PCT Pub. No.: WO91/13856
PCT Pub. Date: Sep. 19, 1991

[30] Foreign Application Priority Data

Mar. 13, 1990 [JP] Japan .................. 2-61756

[51] Int. Cl.$^5$ .............................. C07C 51/16
[52] U.S. Cl. ...................... 562/535; 562/545
[58] Field of Search ................ 562/535, 547

[56] References Cited

U.S. PATENT DOCUMENTS

| | | | |
|---|---|---|---|
| 3,238,253 | 3/1966 | Kerr | 562/535 |
| 3,579,573 | 5/1971 | Gilde et al. | 562/535 |
| 3,875,220 | 4/1975 | White et al. | |

FOREIGN PATENT DOCUMENTS 0071140 2/1983 European Pat. Off. .
0362817 4/1990 European Pat. Off. .

Primary Examiner—José G. Dees
Assistant Examiner—Joseph M. Conrad, III
Attorney, Agent, or Firm—Oblon, Spivak, McClelland, Maier & Neustadt

[57] ABSTRACT

This invention provides a method for producing methacrylic acid by the use of a catalyst having activity for methacrolein oxidation and superior thermal resistance and capable of preparation with good reproducibility.

Methacrylic acid is produced by allowing methacrolein and an oxygen-containing gas to undergo a catalytic gas phase oxidative reaction in the presence of a catalyst containing divanadyl pyrophosphate as an active ingredient. It is allowed that some of the vanadium atoms in the above catalyst are pentavalent or all of the vanadium atoms have been oxidized into pentavalent vanadium ions.

In addition, the above catalyst can be produced from an oxide of vanadium and an oxyacid of phosphorus and has higher catalytic activity when it contains 0.001 to 40 mole % excess phosphorus as calculated in phosphoric acid equivalent. The compound $VO(H_2PO_4)_2$ is preferable for an excess of phosphorus.

7 Claims, No Drawings

METHOD FOR PRODUCING METHACRYLIC ACID

FIELD OF THE INVENTION

This invention relates to a method for producing methacrylic acid, and more specifically to a method for producing methacrylic acid by conducting a catalytic gas phase oxidative reaction of methacrolein by the use of a catalyst containing divanadyl pyrophosphate as an active ingredient.

BACKGROUND ART

Heteropoly-acids such as molybdophosphoric acid and molybdovanadophosphoric acid are known as catalysts used for catalytic gas phase oxidative reactions of methacrolein. However, said heteropoly-acids are thermally unstable and liable to deteriorate. Although an alkali metal or the like can be added to a heteropoly-acid to form an alkali metal salt which has improved thermal resistance, the alkali metal salt exhibits only insufficient catalytic activity and its use results in inferior redox efficiency since catalytic activity for methacrolein oxidation rigidly derives only from free heteropoly-acid.

DISCLOSURE OF THE INVENTION

This invention was achieved by perceiving the above circumstances and its object is to provide a method for producing methacrylic acid by the use of a catalyst free from the above inconveniences and exhibiting catalytic activity for the catalytic gas phase oxidative reaction of methacrolein.

DESCRIPTION OF THE PREFERRED EMBODIMENTS

After intensive researches to develop a catalyst other than catalysts consisting of heteropoly-acids or their salts and having inferior thermal resistance which has activity for the catalytic gas phase reaction of methacrolein, selectivity for methacrylic acid and superior thermal resistance, the inventor found that vanadium-phosphoric acid complex compounds exhibit a superior catalytic activity in the gas phase oxidation of methacrolein and have favorable thermal resistance. Thus this invention was considered.

The above vanadium-phosphoric acid complex compounds consist of vanadyl phosphate which contains pentavalent vanadium and divanadyl pyrophosphate which contains tetravalent vanadium and each of these compounds can be further classified by their crystal structure into several groups. Since divanadyl pyrophosphate has a specially high activity although all these compounds exhibit catalytic activity for methacrolein oxidation, divanadyl pyrophosphate was determined to be the essential active ingredient in the catalyst used in this invention. Therefore, the catalyst used in this invention may consists of the above active ingredient alone as a matter of course or may contain both the above active ingredient and vanadyl phosphate.

A catalyst containing excess phosphorus in addition to divanadyl pyrophosphate or vanadyl phosphate which contains a chemical equivalent amount of phosphorus is more desirable for this invention because the catalytic activity is further increased and the catalyst is not easily oxidized. However, an excessive amount of phosphorus results in excessive oxidation of methacrolein and an increased amount of acetic acid produced as a by-product. Therefore the excess amount of phosphorus is preferably in the range of between 0.001 to 40 mole %, more preferably between 1 and 10 mole %, calculated in phosphoric acid equivalent.

A specially great effect can be achieved by using the aforementioned $VO(H_2PO_4)_2$ for an excess of phosphorus in the catalyst. The above $VO(H_2PO_4)_2$ can easily be produced, for example, by adding to isobutyl alcohol vanadium pentoxide in such an amount that the atomic ratio of phosphorus to vanadium becomes 2.00 and then reducing vanadium pentoxide by passing hydrogen chloride gas through the mixture, followed by adding orthophosphoric acid prior to heating and agitating the mixture under reflux.

Although divanadyl pyrophosphate which contains tetravalent vanadium was mentioned to ve preferable, joint use of this compound with vanadyl phosphate which contains pentavalent vanadium tends to result in increased catalytic activity. In particular, divanadyl pyrophosphate wherein some of the vanadium atoms have been oxidized into pentavalent ones can further increase the catalytic activity. Partial oxidation of the vanadium atoms of divanadyl pyrophosphate can be achieved by heating it in the air at 200° to 700° C.

Divanadyl pyrophosphate used in the present invention may be of either $\alpha$-, $\beta$- or $\gamma$-type and they can easily be produced with good reproducibility by the following method.

Specifically, the recommended method consists of reducing vanadium pentoxide with a reducing agent and then making the reduction product react with orthophosphoric acid to produce a precursor which is then thermally treated. As the above reducing agent, a normal reducing agent such as hydroxylamine hydrochloride, hydrazine or its derivative, an aliphatic alcohol containing 1 to 6 carbon atoms or hydrogen chloride may be used. Divanadyl $\gamma$-pyrophosphate can be produced, for example, by using vanadyl $\alpha$-phosphate dihydrate instead of the above vanadium pentoxide.

The catalyst of this invention, although it can be used as it is, can be made to stick to a carrier with a suitable shape or can be made to stick to or be held by a carrier in a form such as powder, sol or gel. The above carrier may be any publicly known one such as titanium dioxide, silica gel, silica sol, diatomaceous earth, silicon carbide, alumina, silica, silica-alumina, bentonite, graphite, a refractory or zeolite and silica gel or silica sol is most preferable.

Methacrolein used for the catalytic gas phase oxidative reaction of this invention does not necessarily have to be pure and may be one containing impurities and having been produced by a catalytic gas phase oxidative reaction of isobutylene or tertiary butyl alcohol.

A mixed gas containing 0.5 to 10 vol % of the above methacrolein and also containing oxygen in an amount corresponding to 0.5 to 10 molar ratio, preferably 1 to 5 molar ratio, to methacrolein is desirable as the original gas used for the production of methacrylic acid.

Although steam may be present or absent in the original mixed gas, it is preferable that steam be present in an amount corresponding to 0.5 to 10 molar ratio to methacrolein. In addition, it is preferable that the original mixed gas be diluted with an inactive gas such as nitrogen or carbon dioxide. It is also possible to use as a dilution gas the waste gas discharged after the catalytic gas phase oxidative reaction of the this invention as it is or after it is oxidized.

In addition, it is desirable that the above original gas be allowed to undergo a catalytic gas phase oxidative reaction by making the above original gas in contact with the aforementioned catalyst at a temperature between 200° C. and 500° C. under a pressure between normal pressure and 30 kg/cm². The space velocity is preferably in the range between 100 and 5,000 hr$^{-1}$, more preferably in the range between 500 and 2,000 hr$^{-1}$.

EXAMPLES

The present invention will be described in detail by way of the following examples although the present invention is not restricted by these examples.

EXAMPLE 1

Preparation of a catalyst

After 10 g of vanadium pentoxide was added to 80 ml of isobutanol, hydrogen chloride gas was passed through the mixture while agitating it for about five minutes. Next, 11.9 g of 99 wt % orthophosphoric acid was added and the mixture was heated under reflux for one hour. After the resulting solution was heated at 150° to 200° C. for two hours and then at 250° C. for four and a half hours to evaporate it to dryness, the solid product was baked at 350° C. for four and a half hours to produce a precursor. After this precursor was pulverized into a 24 to 35 mesh powder, it was packed in a reaction tube and activated by passing a gas consisting of 3 ml/min. methacrolein, 10 ml/min. oxygen, 20 ml/min. steam and 70 ml/min. helium through the packed powder while maintaining it at 400° C. for four hours to prepare a catalyst (A).

X-ray diffractiometry clarified that the catalyst (A) primarily consisted of $\delta$-(VO)$_2$P$_2$O$_7$. It was seen from the amounts of raw materials used that the catalyst (A) contained 5 mole % excess phosphorus over its amount in divanadyl pyrophosphate as calculated in phosphoric acid equivalent.

Reaction

After 5 g of the catalyst (A) was packed in a flow-type reaction tube, an original gas consisting of 3 ml/min. methacrolein, 10 ml/min. oxygen, 20 ml/min. steam and 70 ml/min. helium was passed through the packed catalyst while maintaining it at 310° C. for four hours. Gas chromatographic analysis of the gaseous product clarified that the conversion of methacrolein was 26.8% and the selectivity for methacrylic acid was 78.1 mole %.

EXAMPLE 2

Preparation of a catalyst

After 10 g of vanadium pentoxide and 54 ml of 85 wt % orthophosphoric acid were added to 100 ml of water and the mixture was refluxed at 100° C. for 16 hours, it was filtered off and washed to produce $\alpha$-VOPO$_4$. 2H$_2$O.

After 200 ml of isobutyl alcohol was added to 10 g of said $\alpha$-VOPO$_4$. 2H$_2$O and the mixture was heated under reflux for six hours prior to its filtration, the resulting solid was mixed with 0.2 g of 85 wt % orthophosphoric acid by well grinding them down and then the mixture was dried at 130° C. The dried mixture was pulverized into a 24 to 35 mesh powder like in Example 1 and then the powder was activated by passing a gas containing methacrolein through it to prepare a catalyst (B).

X-ray diffractiometry clarified that the catalyst (B) primarily consisted of $\gamma$-(VO)$_2$P$_2$O$_7$. It was seen from the amounts of raw materials used that the catalyst (B) contained 9 mole % excess phosphorus over its amount in divanadyl pyrophosphate as calculated in phosphoric acid equivalent.

Reaction

Five grams of the catalyst (B) was used to conduct a catalytic gas phase oxidative reaction of methacrolein in the same manner as in Example 1. Gas chromatographic analysis clarified that the conversion of methacrolein was 40.6% and the selectivity for methacrylic acid was 80.0 mole %.

EXAMPLE 3

Preparation of a catalyst

The precursor obtained in Example 1 was heated in the air at 600° C. for three hours to prepare a catalyst (C). X-ray diffractiometry clarified that in the catalyst (C) some of the vanadium atoms of divanadyl pyrophosphate molecules had been changed into pentavalent ones contained in VOPO$_4$ molecules.

The catalyst (C) contained 5 mole % excess phosphorus over its amount in divanadyl pyrophosphate as calculated in phosphoric acid equivalent.

Reaction

After 5 g of the catalyst (C) was packed in a flow-type reaction tube, an original gas consisting of 3 ml/min. methacrolein, 10 ml/min. oxygen, 20 ml/min. steam and 70 ml/min. helium was passed through the packed catalyst while maintaining it at 310° C. for four hours. Gas chromatographic analysis of the gas discharged from the outlet of the reaction tube clarified that the conversion of methacrolein was 9.1% and the selectivity for methacrylic acid was 82.9 mole %.

EXAMPLE 4

Preparation of a catalyst

After 14.3 g of hydroxylamine hydrochloride and 23.1 g of 85 wt % phosphoric acid were added to 200 ml of distilled water, the mixture was heated to 70° C. to prepare a solution. After 18.4 g of vanadium pentoxide was added to the solution, the mixture was heated at 90° C. while agitating it for one hour to allow a reaction. Next, after the reaction product mixture was evaporated to dryness at 110° C., 100 ml of distilled water was added to the residual solid and the mixture was boiled, the boiled mixture was filtered off, washed with water and dried at 130° C. to produce a light blue solid. The solid was then heated in a nitrogen stream at 550° C. for two hours to prepare a catalyst (D).

X-ray diffractiometry clarified that the catalyst (D) primarily consisted of $\alpha$-(VO)$_2$P$_2$O$_7$. No excess phosphorus over its amount in divanadyl pyrophosphate was contained in the catalyst (D).

Reaction

Five grams of the catalyst (D) was used to conduct a catalytic gas phase oxidative reaction of methacrolein in the same manner as in Example while maintaining the reaction tube at 330° C. Gas chromatographic analysis clarified that the conversion of methacrolein was 25.0% and the selectivity for methacrylic acid was 59.0 mole %.

EXAMPLE 5

Preparation of VO(H$_2$PO$_4$)$_2$

After 10 g of vanadium pentoxide was added to 80 ml of isobutyl alcohol, hydrogen chloride gas was passed through the mixture while agitating it for about five minutes. Following that, 21.8 g of 99 wt % orthophosphoric acid was added and the mixture was heated under reflux for one hour. After the reaction, 100 ml of toluene was added to the reaction product mixture and the resulting mixture was heated to distill away isobutyl alcohol alone. The resulting precipitate in toluene was removed and dried. An X-ray diffraction spectrum of the resulting precipitate had peaks at d levels of 6.34, 3.99, 3.58, 3.37, 3.17 and 2.84 (Å) which are characteristic of VO(H$_2$PO$_4$)$_2$.

Preparation of a catalyst

After 10 g of vanadium pentoxide was added to 80 ml of isobutyl alcohol, hydrogen chloride gas passed through the mixture while agitating it for about five minutes. Next, 10.9 g of 99 wt % orthophosphoric acid was added and the mixture was heated under reflux for one hour. The resulting solution was evaporated to dryness by heating it at 150° to 200° C. for two hours and then at 250° C. for four and a half hours to produce a precursor. Next, after 0.44 g of VO(H$_2$PO$_4$)$_2$ was dissolved in 40 ml of distilled water, the above precursor was added to the solution and the mixture was evaporated to dryness while agitating it. The resulting solid was pulverized into a 24 to 35 mesh powder which was then packed in a reaction tube and activated by passing a gas consisting of 3 ml/min. methacrolein, 10 ml/min. oxygen, 20 ml/min. steam and 70 ml/min. helium through the packed powder while maintaining it at 400° C. for four hours to prepare a catalyst (E).

X-ray diffractiometry clarified that the catalyst (E) primarily consisted of β-(VO)$_2$P$_2$O$_7$. The catalyst (E) contained 6.2 mole % of VO(H$_2$PO$_4$)$_2$ as calculated in phosphoric acid equivalent in addition to (VO)$_2$P$_2$O$_7$.

Reaction

After 5 g of the catalyst (E) was packed in a flow-type reaction tube, an original gas consisting of 3 ml/min. methacrolein, 10 ml/min. oxygen, 20 ml/min. steam and 70 ml/min. helium was passed through the packed catalyst while maintaining it at 300° C. for four hours. Gas chromatographic analysis of the gaseous product clarified that the conversion of methacrolein was 32.0% and the selectivity for methacrylic acid was 78.2 mole %.

EXAMPLE 6

Preparation of a catalyst

After 10 g of vanadium pentoxide and 54 ml of 85 wt % orthophosphoric acid were added to 150 ml of distilled water, the mixture was refluxed at 100° C. for 16 hours and was then filtered off and washed to produce α-VOPO$_4$. 2H$_2$O.

After 200 ml of butyl alcohol was added to 10 g of said α-VOPO$_4$. 2H$_2$O, the mixture was heated under reflux for six hours prior to its filtration to produce a solid, which was found to be VOHPO$_4$. 0.5H$_2$O. Next, after 0.4 g of VO(H$_2$PO$_4$)$_2$ produced in the same manner as in Example 5 was dissolved in 40 ml of distilled water, the above VOHPO$_4$. 0.5H$_2$O was added to the solution and the mixture was dried by heating it while agitating it. Like in Example 1, the resulting substance was pulverized into a 24 to 35 mesh powder which was then activated by passing a gas containing methacrolein through the powder to prepare a catalyst (F).

X-ray diffractiometry clarified that the catalyst (F) primarily consisted of γ-(VO)$_2$P$_2$O$_7$. It was seen from the amounts of raw materials used that the catalyst (F) contained 5.6 mole % of VO(H$_2$PO$_4$)$_2$ as calculated in phosphoric acid equivalent in addition to (VO)$_2$P$_2$O$_7$.

Reaction

Five grams of the catalyst (F) was used to conduct a catalytic gas phase oxidative reaction of methacrolein in the same manner as in Example 5. Gas chromatographic analysis clarified that the conversion of methacrolein was 42.8 mole % and the selectivity for methacrylic acid was 81.2 mole %.

EXAMPLE 7

Preparation of a catalyst

After 0.4 g of VO(H$_2$PO$_4$)$_2$ produced in the same manner as in Example 5 was dissolved in 40 ml of distilled water, β-(VO)$_2$P$_2$O$_7$ produced in the same manner as in Example 5 was added to the solution and the mixture was dried up by distilling away distilled water to make the above VO(H$_2$PO$_4$)$_2$ to be held by the above β-(VO)$_2$P$_2$O$_7$. The thus obtained solid was activated by the method described in Example 1 to prepare a catalyst (G). It was seen from the amounts of raw materials used that the catalyst (G) contained 5.6 mole % of VO(H$_2$PO$_4$)$_2$ as calculated in phosphoric acid equivalent in addition to (VO)$_2$P$_2$O$_7$.

Reaction

Five grams of the catalyst (G) was used to conduct a catalytic gas phase oxidative reaction of methacrolein in the same manner as in Example 5. Gas chromatographic analysis clarified that the conversion of methacrolein was 39.6 mole % and the selectivity for methacrylic acid was 82.0 mole %.

EXAMPLE 8

Preparation of a catalyst

After 2.5 g of vanadium pentoxide was added to 20 ml of isobutyl alcohol, hydrogen chloride gas was passed through the mixture while agitating it for five minutes. Next, 2.73 g of 99 wt % orthophosphoric acid was added and the mixture was refluxed for one hour. The resulting solution was evaporated to dryness by heating it at 150° to 200° C. for two hours and then at 250° C. for four hours to produce a precursor.

Next, after 0.11 g of VO(H$_2$PO$_4$)$_2$ produced in the same manner as in Example 5 was dissolved in 10 ml of distilled water and the above precursor was added to the solution, 30 g of 20% silica sol was added and the mixture was evaporated to dryness while agitating it. After the resulting solid was pulverized into a 34 to 35 mesh powder and it was packed in a reaction tube, the packed powder was activated by passing a gas consisting of 3 ml/min. methacrolein, 10 ml/min. oxygen, 20 ml/min. steam and 70 ml/min. helium through the packed powder while maintaining it at 400° C. for four hours to prepare a catalyst (H). X-ray diffractiometry clarified that the main active ingredient of the above catalyst (H) was β-(VO)$_2$P$_2$O$_7$. The catalyst (H) contained 6.2 mole % of VO(H$_2$PO$_4$)$_2$ as calculated in phosphoric acid equivalent in addition to (VO)$_2$P$_2$O$_7$.

Reaction

Five grams of the catalyst (H) was used to conduct a catalytic gas phase oxidative reaction of methacrolein in the same manner as in Example 5. Gas chromatographic analysis clarified that the conversion of methacrolein was 39.6 mole % and the selectivity for methacrylic acid was 75.2 mole %.

INDUSTRIAL APPLICABILITY

According to this invention, it is possible to provide a method for producing methacrylic acid by the use of a catalyst having activity for methacrolein oxidation and superior thermal resistance and capable of preparation with high reproducibility.

I claim:

1. A method for producing methacrylic acid by allowing methacrolein to undergo a catalytic gas phase oxidation in the presence of a catalyst, in which the catalyst contains divanadyl pyrophosphate as an active ingredient, wherein the catalyst contains 0.001 to 40 mol % excess phosphorus as calculated in phosphoric acid equivalent.

2. A method for producing methacrylic acid by using a catalyst according to claim 1 which is produced from an oxide of vanadium and an oxyacid of phosphorus.

3. A method for producing methacrylic acid as set forth in claim 1, wherein the catalyst contains the compound $VO(H_2PO_4)_2$ for an excess of phosphorus.

4. A method for producing methacrylic acid as set forth in claim 3, wherein some of the vanadium atoms in the catalyst are pentavalent vanadium ions.

5. A method for producing methacrylic acid as set forth in claim 4, wherein the catalyst contains as an active ingredient divanadyl pyrophosphate wherein the vanadium atoms have been oxidized into pentavalent vanadium ions.

6. A method for producing methacrylic acid as set forth in claim 1, wherein some of the vanadium atoms in the catalyst are pentavalent vanadium ions.

7. A method for producing methacrylic acid as set forth in claim 1, wherein the catalyst contains as an active ingredient divanadyl pyrophosphate wherein the vanadium atoms have been oxidized into pentavalent vanadium ions.

* * * * *